United States Patent [19]
Obermayer et al.

[11] Patent Number: 5,180,821
[45] Date of Patent: Jan. 19, 1993

[54] CYCLIC TETRABENZIMIDAZOLE

[75] Inventors: Arthur S. Obermayer, Newton; James B. Hendrickson; Sajjat Hussoin, both of Cambridge, all of Mass.

[73] Assignee: Moleculon Research Company, Newton, Mass.

[21] Appl. No.: 847,835

[22] Filed: Mar. 9, 1992

Related U.S. Application Data

[63] Continuation of Ser. No. 725,883, Jun. 28, 1991, abandoned, which is a continuation of Ser. No. 464,998, Jan. 16, 1990, abandoned.

[51] Int. Cl.$^5$ .......................................... C07D 233/54
[52] U.S. Cl. .................................... 540/465; 540/472; 540/476
[58] Field of Search .................. 540/472, 476, 465

[56] References Cited

U.S. PATENT DOCUMENTS 3,481,945  12/1969  Nichols et al. ...................... 260/299

Primary Examiner—Nicholas S. Rizzo
Attorney, Agent, or Firm—Iandiorio & Dingman

[57] ABSTRACT

Cyclic tetrabenzimidazole, a yellowish, visually non-fluorescent substance, and its chelates, tautomers, ionization and oxidation forms, having utility as chelating agents, catalysts and electrooptic components.

2 Claims, 1 Drawing Sheet

CYCLIC TETRABENZIMIDAZOLE

This is a continuation of application Ser. No. 07/725,883, filed Jun. 28, 1991 now abandoned which is a continuation of Ser. No. 464,998 filed Jan. 16, 1990, now abandoned.

FIELD OF INVENTION

This invention relates to tetrabenzimidazole, and more particularly to cyclic tetrabenzimidazole, a yellowish substance useful as a chelating agent, catalyst and an electrooptic component.

BACKGROUND OF INVENTION

In U.S. Pat. No. 3,481,945, tetrabenzimidazole, tetrabenzothiazole and tetrabenzoxazole were described and claimed. A single example of a method of producing the compound was detailed. In that method, 2,3-diaminobenzoic acid was refluxed with meta-cresol and a copper compound to form a dark substance having a melting point above 400° C. The substance was described as copper tetrabenzimidazole, a chelate. The properties of the isolated compound were described in depth; an acidic solution was strongly colored, and both acidic and neutral solutions exhibited strong fluorescence when excited by visible light.

However, it was recently determined that the substance produced by following the method disclosed in the patent was not copper tetrabenzimidazole, but rather the well known compound fluorindine (5,12-dihydroquinoxalo[2,3-b]phenazine). The error was discovered when mass spectrometry work on the isolated substance indicated that the substance had the empirical formula of fluorindine. A sample of fluorindine was then prepared by an established synthetic process; that sample had properties identical to those of the compound isolated by the method disclosed in the patent. Thus, the substance isolated and described in the patent is fluorindine, not copper tetrabenzimidazole.

SUMMARY OF INVENTION

It is therefore an object of this invention to provide a novel cyclic tetrabenzimidazole.

It is a further object of this invention to provide an aromatic compound having a cyclic structure.

It is a further object of this invention to provide a compound useful as a chelating agent, a catalyst and an electrooptic component.

It is a further object of this invention to provide a novel synthetic approach to yield a compound with the structure of tetrabenzimidazole but with unexpected properties.

This invention may be accomplished in a cyclic tetrabenzimidazole, a yellowish, visually non-fluorescent solid having a molecular weight of approximately 464, a melting point above 350° C., slight solubility in a 1:1 mixture of ethanol and chloroform, and IR absorption in potassium bromide at 1620, 1550, 1450, 1400 and 1260 $cm^{-1}$, and the tautomers, oxidation, ionization and chelation forms thereof.

DISCLOSURE OF PREFERRED EMBODIMENT

Other objects, features and advantages will occur from the following description of a preferred embodiment and the accompanying drawings, in which.

Cyclic tetrabenzimidazole is an aromatic compound which from a structural standpoint appears to be similar to phthalocyanines and porphyrins. Because of its four external and four internal imidazole nitrogens, tetrabenzimidazole can have a number of tautomers, with the protons in the center or on the periphery of the ring. These forms can chelate zero, mono, di, tri and tetravalent atoms, and complex with atoms in its various states of oxidation and ionization. Cyclic tetrabenzimidazole possesses two additional oxidized forms, with two and zero imidazole protons. The partially oxidized form has its own amphoteric and tautomeric properties.

Figure 1:
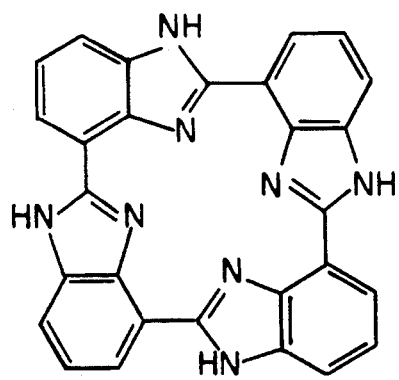
FIG. 1 is a schematic plane formula drawing of the cyclic tetrabenzimidazole according to this invention.

There is shown in FIG. 1 the cyclic tetrabenzimidazole according to this invention. The compound is characterized by four internal and four external nitrogens. The four protons attached to the nitrogen atoms can be in any of the possible tautomeric forms, i.e. internal or external, so long as it is sterically possible. Furthermore, as a result of the amphoteric properties of benzimidazoles, any or all of the four protons can be removed to form negatively charged ions, or alternatively up to four protons can be added to the imide nitrogens to form positively charged ions (so long as steric hindrance does not prevent this proton addition). The molecule can form up to four coordinate bonds with atoms such as metals; it can chelate zero to tetravalent atoms.

The ionization, chelation, tautomeric and oxidation forms of tetrabenzimidazole are identical to tetrabenzimidazole itself except for the removal or addition of the hydrogen atoms or nitrogen atoms or the attachment of a complexing atom to the four internal nitrogen atoms.

The compound exhibits additional oxidation states with two and zero imidazole protons. These oxidation states have the same empirical formulas as anions but with fewer available electrons. The chelates can form both anions and cations in acidic or basic solutions respectively.

The pale color of tetrabenzimidazole is quite surprising and unexpected: previously, a visually fluorescent compound had been expected. Even though tetrabenzimidazole has the same internal cruciform structure as porphorins, it does not have the same high electron mobility and delocalization within the large ring structure and therefore it does not have the intense color and longer wave length color characteristic of porphorins. Furthermore, its spectral properties are very different from those of the phthalocyanine family of compounds even though its structure has many similarities—in particular the large similarly spaced ring structure which also includes a number of aromatic rings and eight nitrogen atoms. Molecular models of tetrabenzimidazole indicate it could be planar but the pale yellow to colorless character of the compound indicates that there is minimal electron delocalization beyond individual benzimidazole rings and therefore the compound would not be required to be in planar form. Molecular orbital calculations also indicate that there is not macrocyclic electron delocalization.

The cyclic tetrabenzimidazole may be prepared from 2,3-diaminobenzoic acid. a monomer having a single carboxy group and two amino groups on a benzene ring:

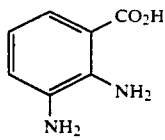

The monomer may be synthesized by traditional methods, for example as disclosed by Chapman and Stephen, *J. Chem. Soc.*, 1925, 1791. The overall synthetic approach for the cyclic tetrabenzimidazole contemplates the production from the monomer of linear dimers, coupled to form a linear tetramer, which is cyclized as a last step.

45 grams of 2,3-diaminobenzoic acid was suspended in 500 ml of chloroform, to which was slowly added 15 ml of triethylamine. After cooling with an ice water bath, 150 ml of thionyl chloride was added dropwise. The reddish-brown solution was refluxed for one hour. After cooling, the reaction mixture was poured into water to destroy excess thionyl chloride, and washed with water and a saturated sodium chloride solution (brine). The organic layer was dried over magnesium sulfate, and evaporated. Sublimation afforded in 75% yield the acid chloride as pale yellow crystals, mp 117° C.:

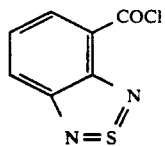

The acid chloride was then hydrolyzed with base to form the thiadiazole acid. 39.7 9 of the acid chloride was suspended in 500 ml of 10% potassium hydroxide and refluxed for 30 minutes. After total dissolution, the reaction mixture was filtered, cooled and acidified with 10% hydrochloric acid. The precipitate was centrifuged, washed with water and dried in a vacuum oven to give in 78% yield off-white crystals of the thiadiazole acid, mp 175°-177° C.:

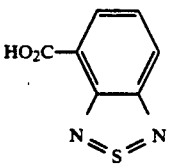

The second element for production of the dimer, the ester of 2,3-diaminobenzoic acid, was formed by suspending 45 g of the diaminobenzoic acid in 500 ml of absolute ethanol. After addition of 20 ml of concentrated sulfuric acid, the reaction mixture was refluxed for 72 hours. The ethanol was stripped off and the residual oil dissolved in water and neutralized with concentrated ammonium hydroxide to pH 8. The white suspension was stirred with hot methylene chloride for 30 minutes, filtered through celite, and washed several times with hot methylene chloride. The methylene chloride fraction was twice washed with water, and brine. dried over anhydrous magnesium sulfate, and evaporated under reduced pressure to afford in 78% yield the ester as a crystalline solid, mp 60°-70° C.:

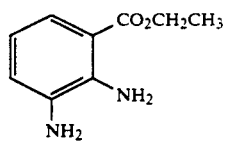

The ester and acid were then coupled to form the benzimidazole ester dimer by cyclodehydration. A solution of 120 g of N-diphenylphosphinyl-N'-methylpiperazine in 500 ml of methylene chloride was chilled to 0° C. A solution of 33.64 ml of triflic anhydride in 200 ml of methylene chloride was added dropwise. After 15 minutes, a mixture of 18 g of the thiadiazole acid and 18 g of the diamino ester was added, and the mixture was stirred at room temperature for twenty minutes. After filtration and solvent evaporation, the semi-solid residue was washed with a copious amount of water and 10% potassium bicarbonate, again washed with water, dried, and recrystallized from heptane to give in approximately 55% yield the benzimidazole ester dimer as yellow crystals, mp 172°-173° C.:

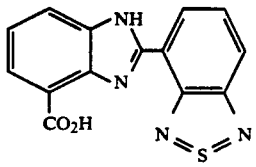

After several days the mother liquor yielded another approximately 30% of the dimer for a total yield of 85%.

The next steps in the synthesis comprised the production of the acid and diamino ester forms of the dimer, which were then coupled into the linear tetramer. The benzimidazole acid dimer was prepared by suspending 6.48 g of the ester dimer in 200 ml of 10% potassium hydroxide with a few drops of ethanol, and refluxing for an hour. After cooling, the solution was made slightly acidic by dropwise addition of concentrated hydrochloric acid. The bright yellow precipitate was centrifuged, washed with water, filtered, and dried in a vacuum oven to give in 88% yield the acid dimer as bright yellow crystals, mp over 300° C.

The diamino ester dimer was prepared by suspending 6.48g of the ester dimer and 130 g of anhydrous stannous chloride in 250 ml of absolute ethanol, and passing anhydrous hydrogen chloride gas through to make a clear solution. After four hours of reflux, the resulting green solution was distilled under vacuum to remove the solvent. The solid residue was dissolved in water, made basic with concentrated ammonium hydroxide, and the resulting yellowish-white slurry was filtered through celite and washed with water. The residue was washed repeatedly with methylene chloride, and the light green solution was twice washed with water and then brine, and dried over anhydrous magnesium sulfate. After evaporation, light yellow crystals were left. Thin layer chromatographic analysis on silica (2:1 hexane:ethyl acetate) left a residue at the origin, with a single compound of lower Rf. A solution of the crystals in methylene chloride was passed through a column of silica (2:1 hexane:ethyl acetate) and on evaporation left in 85% yield the diamino ester dimer as clean yellow crystals which darkened on standing in air, mp 106°–107° C.:

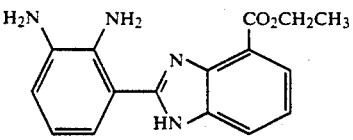

The next step was to couple by cyclodehydration the diamino ester and acid dimers to form a protected linear tetramer. A solution of 13.5 g of N-diphenylphosphinyl-N'-methylpiperazine in 100 ml of methylene chloride at 0° C. was prepared, to which was added dropwise a solution of 16.82 ml of triflic anhydride in 100 ml of methylene chloride. After 15 minutes a mixture of 2.96 g of the benzimidazole acid dimer and 2.96 g of the diamino ester dimer was added and stirred for two hours at room temperature. After filtration and solvent evaporation, the semi-solid residue was thoroughly washed with water and 10% potassium hydroxide solution, water again, and then toluene. The residue was then recrystallized from hot ethanol leaving in 60% yield the diamino protected tetramer ester as bright yellow crystals, mp 240°–244° C.:

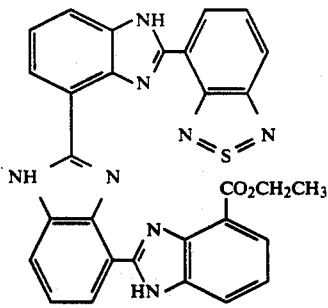

The next step was to deprotect the diamino functions by reduction of the thiadiazole. This was accomplished as before, by suspending 1.11 g of the protected tetramer ester and 22.2 g of anhydrous stannous chloride in 100 ml of ethanol, and passing through enough anhydrous hydrogen chloride gas to make a clear solution. The resulting off-red solution was refluxed for four hours and distilled under reduced pressure to remove the solvent. The solid residue was suspended in water, made basic by the addition of concentrated ammonium hydroxide, and the resulting white slurry was filtered through celite and washed with water. The residue was washed repeatedly with a 1:1 mixture of chloroform and methanol until no color came through. The light yellow solution was concentrated under reduced pressure and held in a freezer overnight. After the addition of a small amount of methanol, the white tin hydroxide precipitate was filtered off. On evaporation, the solution left in 84% yield the tetramer diamino ester as bright yellow crystals, mp 269°–270° C.:

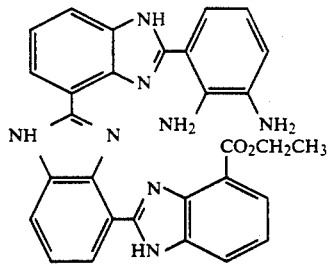

The crystals darken on standing in air; they are best kept in the freezer under nitrogen.

The final step in synthesis of the cyclic product was accomplished by heating 264 mg of the tetramer diamino ester neat at 300° C. in a sand bath for 15 minutes under nitrogen. Chromatographic analysis on reverse phase silica, with 3:1 acetonitrile:ethyl acetate, revealed disappearance of the starting material. The resulting dark brown solid was refluxed for one hour with 150 ml of a 1:1 mixture of chloroform and ethanol, filtered hot through celite, and washed with the same solvent. On evaporation, there was left 195 mg of fine light yellow crystals, mp>350° C. The crystals were extremely insoluble, with only slight solubility in a 1:1 mixture of chloroform and ethanol, and exhibited no ester carbonyl in the IR spectrum. The mass spectrum showed the expected peak at m/e 464. Although the crystals were lightly colored, they exhibited no fluorescence when excited by visible light.

The $^1$H NMR (DMSO-$d_6$) showed four multiple peaks at: 8.5–8.2, 8.1–7.7, 7.6–7.2 and 6.8–6.5. The integrated areas were in the ratio 3:8:4:3, respectively. The $^{13}$C NMR(DMSO-$d_6$) showed six broad peaks at : 153.2, 136.5, 132.3, 128.3, 124.3, and 115.4. The crystals were then sublimed in a sand bath above 350° C. and under a high vacuum to provide a 7% yield cyclic tetrabenzimidazole as yellowish crystals. The IR spectrum (in potassium bromide) remained as before sublimation:absorption at 1620, 1550, 1450, 1400 and 1260 cm$^{-1}$, although the subliminal product was generally cleaner in appearance.

Although the cyclic tetrabenzimidazole was synthesized from the 2,3-diaminobenzoic acid monomer in a stepwise fashion, the cyclic tetramer may likely be produced in a single self-condensation reaction employing a dilute solution of the monomer or related compounds.

Figure 2A:
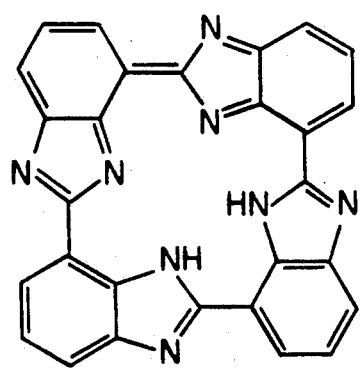
FIGS. 2A and 2B are drawings of tautomers of an oxidized form of the cyclic tetrabenzimidazole of FIG. 1.
Figure 2B:
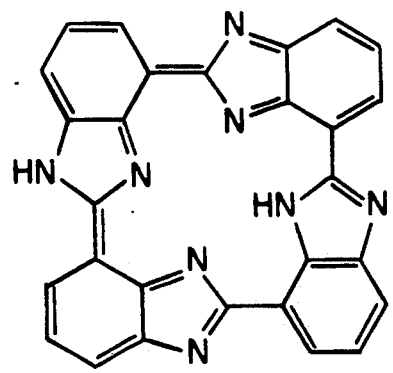
Figure 3:
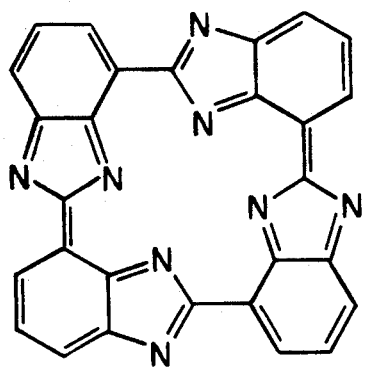
FIG. 3 is a drawing of a further oxidized form of the cyclic tetrabenzimidazole of FIG. 1.
Figure 4:
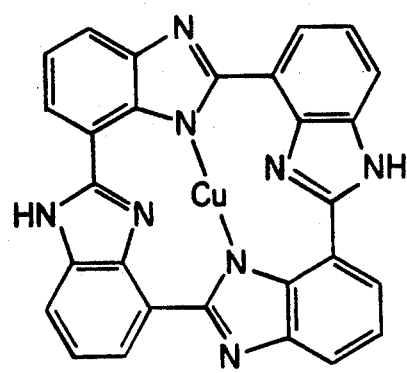
FIG. 4 is a drawing of a copper chelate of the cyclic tetrabenzimidazole of FIG. 1.

FIGS. 2A and 2B depict tautomers of a partially oxidized form of the cyclic tetrabenzimidazole according to this invention. These forms show delocalization throughout the macrocyclic structure and therefore should be highly colored. FIG. 3 depicts the fully oxidized form which has no tautomers because of the lack of hydrogens on the nitrogens, but is structurally similar to the tetranegative ion of the unoxidized form with the exception of having four less electrons in its structure. These forms should be intensely colored. A copper chelate is shown in FIG. 4. The chelates can form cationic and anionic species in acidic and basic solutions.

A copper complex of the cyclic tetrabenzimidazole product was prepared from a mixture of 116 mg of cyclic tetrabenzimidazole and 1 g of copper (II) acetate monohydrate, heated in a sand bath at 300° C. for 30 minutes. The brown solid was washed with 10% hydrochloric acid and water, and dried in a vacuum oven to give 150 mg of pale yellow crystals, mp greater than 350° C. The IR spectrum of the crystals was similar to the starting cyclic tetrabenzimidazole; absorption at 1620, 1450, 1260, 1320, 1275, 1050 and 750 cm$^{-1}$. After sublimation above 350° C. under high vacuum, the pale yellow crystals afforded in 15% yield the copper complex as colorless crystalline plates. The IR spectrum yielded peaks at 1430, 1410, 1330, 1300, 1125, 940, 760 and 700 cm$^{-1}$; the 1620 cm$^{-1}$ peak was lacking.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A yellowish, visually non-fluorescent compound having the formula:

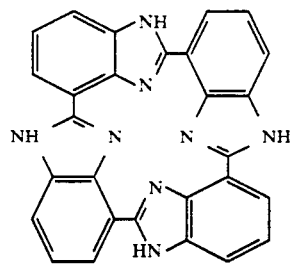

and the tautomers, oxidation, ionization and chelation forms thereof.

2. A yellowish, visually non-fluorescent substance having a molecular weight of approximately 464, a melting point greater than 350° C., slight solubility in a 1:1 mixture of ethanol and chloroform, and exhibiting characteristic absorption bands in the infra red region of the spectrum when in potassium bromide at the following frequencies expressed in reciprocal centimeters: 1620, 1550, 1450, 1400 and 1260, and the tautomers, oxidation, ionization and chelation forms thereof.

* * * * *